(12) United States Patent
Kshirsagar et al.

(10) Patent No.: US 8,748,604 B2
(45) Date of Patent: Jun. 10, 2014

(54) PROCESS FOR STEREOSELECTIVE SYNTHESIS OF 5-FLUORO-1-(2R,5S)-[2-(HYDROXYMETHYL)-1,3-OXATHIOLAN-5-YL]CYTOSINE

(75) Inventors: Prakash Bhimaji Kshirsagar, Pune (IN); Satish Manohar Bhoge, Ahmednagar (IN); Santosh Richhariya, Sagar (IN); Kaptan Singh, Ghaziabad (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 13/582,513

(22) PCT Filed: Feb. 25, 2011

(86) PCT No.: PCT/IB2011/050824
§ 371 (c)(1),
(2), (4) Date: Oct. 24, 2012

(87) PCT Pub. No.: WO2011/107920
PCT Pub. Date: Sep. 9, 2011

(65) Prior Publication Data
US 2013/0072681 A1 Mar. 21, 2013

(30) Foreign Application Priority Data
Mar. 4, 2010 (IN) .............................. 489/DEL/2010

(51) Int. Cl.
*C07D 239/22* (2006.01)

(52) U.S. Cl.
USPC ......................................................... 544/317

(58) Field of Classification Search
USPC ......................................................... 544/317
See application file for complete search history.

(56) References Cited

U.S. PATENT DOCUMENTS

| | | | | |
|---|---|---|---|---|
| 6,051,709 A | * | 4/2000 | Goodyear et al. | ............ 544/314 |
| 7,534,885 B2 | * | 5/2009 | Bertolini et al. | ............ 544/317 |

FOREIGN PATENT DOCUMENTS

| WO | WO 92/20669 | 11/1992 | ........... C07D 327/04 |
|---|---|---|---|
| WO | WO 95/29174 | 11/1995 | ........... C07D 327/04 |
| WO | WO 2004/085432 | 10/2004 | ........... C07D 411/04 |
| WO | WO 2007/077505 A2 * | 7/2007 | ........... C07D 411/04 |
| WO | WO 2009/084033 | 7/2009 | ........... C07D 411/04 |

OTHER PUBLICATIONS

Eller, K., Henkes, E., Rossbacher, R. and Höke, H. 2000. Amines, Aliphatic. Ullmann's Encyclopedia of Industrial Chemistry.*
Goodyear et al., "Practical enantioselective synthesis of lamivudine (3TC™) via a dynamic kinetic resolution", *Tetrahedron Letters*, 46(49):8535-8538 (2005).

* cited by examiner

*Primary Examiner* — Golam M M Shameem
*Assistant Examiner* — Laura Daniel

(57) ABSTRACT

The present invention provides an improved process for stereoselective preparation of 5-fluoro-1-(2R,5S)-[2-(hydroxymethyl)-1,3-oxathiolan-5-yl]cytosine and pharmaceutically acceptable salts thereof.

17 Claims, No Drawings

PROCESS FOR STEREOSELECTIVE SYNTHESIS OF 5-FLUORO-1-(2R,5S)-[2-(HYDROXYMETHYL)-1,3-OXATHIOLAN-5-YL]CYTOSINE

FIELD OF THE INVENTION

The present invention provides an improved process for stereoselective preparation of 5-fluoro-1-(2R,5S)-[2-(hydroxymethyl)-1,3-oxathiolan-5-yl]cytosine and pharmaceutically acceptable salts thereof.

BACKGROUND OF THE INVENTION

Nucleosides, their analogues and derivatives are an important class of therapeutic agents. A number of nucleoside analogues such as 3'-azido-3'-deoxythymidine (AZT), 2'3'-dedeoxy-cytidine (DDC), 1-[2-(hydroxymethyl)-1,3-oxathiolan-5-yl]cytosine, 5-fluoro-1-[2-(hydroxymethyl)-1, 3-oxathiolan-5-yl]cytosine and 2-hydroxymethyl-4-(guanin-9'-yl)-1,3-dioxalane have shown antiviral activity against retroviruses such as human immunodeficiency virus, human B virus and human T-lymphotropic virus.

Emtricitabine also known as FTC, chemically designated as 5-fluoro-1-(2R,5S)-[2-(hydroxymethyl)-1,3-oxathiolan-5-yl]cytosine (Formula I), is a synthetic nucleoside analog having activity against human immunodeficiency virus type 1 (HIV-1) reverse transcriptase.

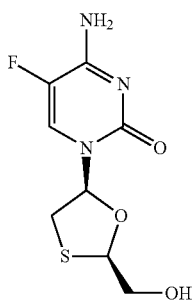

Formula I

Emtriva® (Emtricitabine) is indicated in combination with other antiretroviral agents for the treatment of HIV-1 infection. It contains two chiral centers and exists in the form of two pairs of optical isomers (i.e., two cis-configurations and two in the trans-configuration). However, cis (2R,5S) isomer exhibits higher biological activity as compared to its trans counterpart. Several stereoselective processes employing chiral auxiliaries have been developed to selectively obtain the cis (2R,5S) isomer.

WO 92/20669 provides a process for preparing cis nucleosides (including emtricitabine), involving condensation of L-menthyl cis-1,3-oxathiolan-5S-acetoxy-2R-carboxylate with 5-fluorocytosine in the presence of Lewis acid and reduction of L-menthyl 1,3-oxathiolan-5S-(5-fluorocytosin-1-yl)-2R-carboxylate (referred to as menthyl emtricitabine) so formed in a polar solvent. Owing to the high solubility of emtricitabine in polar solvents, its isolation from this medium poses practical problems and restricts the viability of this process on commercial scale.

WO 95/29174 provides a process for preparing cis nucleoside analogues in which L-menthyl cis-1,3-oxathiolan-5-yl-2R-carboxylate derivative is condensed with 5-fluorocytosine in the absence of Lewis acid to afford L-menthyl 1,3-oxathiolan-5S-(5-fluorocytosin-1-yl)-2R-carboxylate. It further provides a process for isolation of such nucleoside analogues in the form of salts. It specifically exemplifies the isolation of lamivudine, a defluoro analogue of emtricitabine as its salicylate. However, it has been found subsequently that the process gives desired results for lamivudine but is found to be completely inapplicable for emtricitabine. For example, WO 2004/085432 provides a process for isolating oxalate salt of L-menthyl 1,3-oxathiolan-5S-(5-fluorocytosin-1-yl)-2R-carboxylate which upon reduction gives emtricitabine free base in low yields.

WO 2009/084033 provides a process, which involves reducing L-menthyl 1,3-oxathiolan-5S-(5-fluorocytosin-1-yl)-2R-carboxylate and isolating emtricitabine as a salt which upon treatment with organic base gives emtricitabine free base in low yields.

Hence, the present inventors felt a need for developing a commercially viable stereoselective process for the preparation of emtricitabine which achieves high performance, high yield, with reduced complexity cost, by eliminating cumbersome chromatographic steps for purification.

SUMMARY OF THE INVENTION

The present invention provides an improved process for stereoselective preparation of 5-fluoro-1-(2R,5S)-[2-(hydroxymethyl)-1,3-oxathiolan-5-yl]cytosine and pharmaceutically acceptable salts thereof.

The first aspect of the present invention provides a process for the preparation of emtricitabine of Formula I, comprising the steps of:

(a) salifying the compound of Formula II,

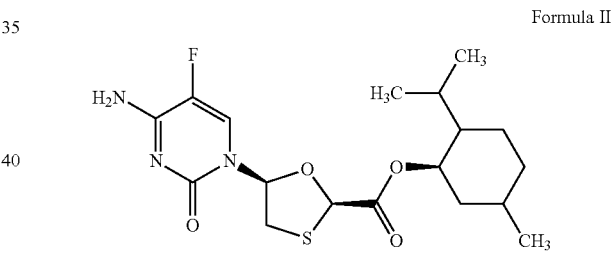

Formula II (b) reducing the salt obtained in step (a);
(c) isolating emtricitabine as a salt;

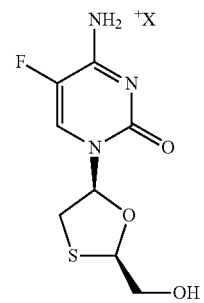

Formula III wherein, 'X' is anion of an acid,
(d) recovering emtricitabine free base.

A second aspect of the present invention provides a process for the preparation of emtricitabine of Formula I, comprising the steps of:

(a) reacting 5-fluorocytosine derivative of Formula IV,

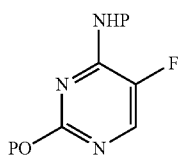

Formula IV wherein 'P' is hydrogen or protecting group,
with a 1,3-oxathiolane derivative of Formula V,

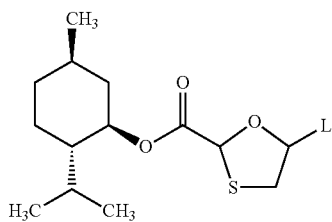

Formula V wherein 'L' is a leaving group,
to give a compound of Formula II,

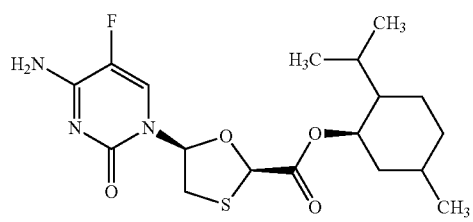

Formula II (b) salifying the compound of Formula II;
(c) reducing the salt obtained in step (b);
(d) isolating emtricitabine as its salt;

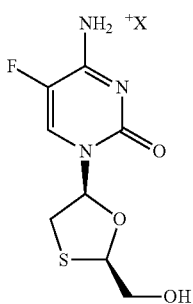

Formula III wherein, 'X' is anion of an acid,
(e) recovering emtricitabine free base.

Other objects, features, advantages and aspects of the present invention will become apparent to those of ordinary skill in the art from the following detailed description.

DETAILED DESCRIPTION OF THE INVENTION

Various embodiments and variants of the present invention are described hereinafter.

A compound of Formula II can be prepared using process(es) known to a person of ordinary skill in the art, for example as cited in WO 92/20669; WO 95/29174 or WO 2004/085432. For instance, the compound of Formula II can be prepared by reacting fluorocytosine derivative of Formula IV,

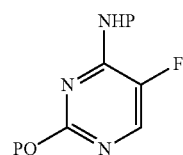

Formula IV wherein 'P' is hydrogen or protecting group, with oxathiolane derivative of Formula V,

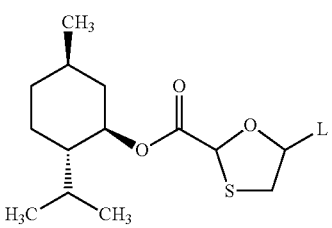

Formula V wherein 'L' is a leaving group, in the presence of one or more base, wherein the base is selected from organic base such as triethylamine in a solvent selected from chlorinated compounds such as dichloromethane.

The leaving group 'L' refers to an atom or a group of atoms which can be displaced upon reaction with an appropriate pyrimidine base. Suitable leaving groups include acyloxy groups, alkoxy groups, alkoxy carbonyl groups (e.g., ethoxy carbonyl or the likes); halogens (e.g., iodine, bromine, chlorine or fluorine); amido; azido; isocyanato; substituted or unsubstituted thiolates (e.g., thiomethyl or thiophenyl); substituted or unsubstituted saturated or unsaturated seleno, seleninyl or selenonyl (e.g., phenyl selenide or alkyl selenide).

The protecting group 'P' refers to a group attached to the main functional groups requiring protection in organic synthesis and is well known to those skilled in art. Suitable protecting groups include trimethyl silyl, dimethyl-t-hexylsilyl, t-butyldimethylsilyl and t-butyldiphenylsilyl, trityl, alkyl groups, acyl groups (e.g., acetyl, propionyl or butyryl), methanesulfonyl or p-toluenesulfonyl.

5-fluoro-N-(trimethylsilyl)-2-[(trimethylsilyl)oxy]pyrimidin-4-amine prepared by the reaction of 5-fluorocytosine with hexamethyldisilazane in the presence of ammonium sulphate is reacted with L-menthyl cis-1,3-oxathiolan-5S-chloro-2R-carboxylate in dichloromethane to obtain a compound of Formula II. The reaction may be carried out in the presence of an organic base such as triethylamine.

According to one embodiment, the compound of Formula II is salified and then converted to a salt of emtricitabine by the steps of basifying followed by in situ reduction and salification under suitable conditions.

The term "suitable conditions" as used herein refers to those reaction conditions known and understood by a person skilled in the art, needed to accomplish the recited reaction or transformation including those described herein.

The terms salified and "salification" used herein refer to the process for preparing salt of a compound using an acid, wherein the acid can be selected from inorganic acid (e.g., hydrochloric acid, hydrobromic acid, hydroiodic acid or the like) or organic acid (e.g., acetic acid, lactic acid, salicylic acid citric acid, oxalic acid, tartraric acid, pantothenoic acid, bitartraric acid, ascorbic acid, succinic acid, maleic acid, fumaric acid, gluconic acid, glucaronic acid, saccharic acid, formic acid, benzoic acid, glutamic acid, methanesulfonic acid, ethanesulfonic acid, benzensulfonic acid, p-toluenesulfonic acid or camphor sulfonic acid).

The term "basifying" as used herein refers to the treatment of the said salt with a base in a suitable solvent, wherein the base is selected from organic base (e.g., triethylamine, isopropylethylamine or diisopropylamine), inorganic base (e.g., sodium carbonate, potassium carbonate, sodium bicarbonate or potassium bicarbonate) or a mixture thereof. The solvent used in this step can be selected from $C_3$-$C_6$ ketones (e.g., acetone, methyltertiary butyl ketone or the like), chlorinated hydrocarbons (e.g., dichloromethane, 1,2-dichloroethane or the like), $C_3$-$C_6$ esters (e.g., methyl acetate, ethyl acetate or a mixture thereof), $C_2$-$C_6$ alcohols (e.g., methanol, ethanol (de-natured spirit), propanol, isopropanol or butanol, tertiary butanol), $C_2$-$C_7$ ethers (e.g., diethylether, methyl tertiary butyl ether, tetrahydrofuran or dioxane), polar aprotic solvents (e.g., dimethylacetamide, dimethylsulfoxide, dimethylformamide, N-methylpyrrolidine), nitriles (e.g., acetonitrile or the likes), water or a mixture thereof.

The reduction step can be carried out using a reducing agent in a solvent selected from $C_5$-$C_8$ aliphatic or aromatic hydrocarbon, $C_2$-$C_6$ alcohols (e.g., methanol, ethanol (denatured spirit), propanol, isopropanol or butanol, tertiary butanol), $C_2$-$C_7$ ethers (tetrahydrofuran, dioxane or diethylether), water or a mixture thereof in the presence of phosphate or borate buffers. The reducing agent used in this step can be selected from metal hydride reagents (e.g., lithium aluminum hydride, lithium borohydride, sodium borohydride or the like) or boranes (diisoamylborane or the like).

The term "isolating" as used herein refers to techniques known to the a person skilled in the art to separate solid compound from the solution, such as decanting, precipitating, filtering, centrifuging, evaporating, distilling, cooling or concentrating the solvent to obtain solid compound. In a preferred experimental procedure, the solution or a suspension containing the product is cooled to a temperature range of 5° C. to 35° C. and the precipitates are filtered to obtain solid compound.

The compound of Formula II, isolated as an oxalate salt is basified using an aqueous solution of sodium carbonate, reduced using sodium borohydride in de-natured spirit in the presence of dipotassium hydrogen phosphate and treated with isopropyl alcohol saturated with hydrochloric acid to give emtricitabine hydrochloride.

Emtricitabine is recovered from its salt by treatment with one or more bases selected from organic base (e.g., triethylamine, isopropylethylamine, diisopropylamine or tri-n-butylamine), inorganic base (e.g., sodium carbonate, potassium carbonate, sodium bicarbonate or potassium bicarbonate) or a mixture thereof.

The term "recovering" as used herein refers to suitable techniques and conditions used to obtain a compound from its reaction mixture such as decanting, filtering, precipitating, centrifuging, cooling, concentrating or evaporating optionally followed by drying.

The term "drying" as used herein refers to the suitable techniques and conditions used to make a compound free from any solvent or moisture such as air drying, vacuum drying or spray drying. Drying can be carried out at room temperature or at elevated temperature.

The present invention also provides substantially pure emtricitabine and pharmaceutically acceptable salts thereof.

The term substantially pure as used herein, can be referred to emtricitabine or pharmaceutically acceptable salts thereof having 99.0%, or particularly 99.5% and most suitably 99.9% or more as measured by HPLC area percentage.

The term room temperature refers to the temperature range of 25° C. to 35° C.

The term "about" as used herein refers to ±10% variation in the values mentioned herein.

The pH of the reaction mixture can be adjusted either by using an acid selected from inorganic acids (e.g., hydrochloric acid or sulfuric acid), organic acid (e.g., acetic acid), inorganic base (e.g., metal carbonates such as sodium carbonate or potassium caronate or metal bicarbonates such as sodium bicarbonate or potassium bicarbonate) or organic base (e.g., triethylamine).

Having thus described the invention with reference to the particular embodiment and illustrative examples, those skilled in the art can appreciate the modifications to the invention as described and illustrated that do not depart from the spirit and the scope of the invention as disclosed in the specifications.

Non limiting examples of the present invention are as follows.

EXAMPLES

Example 1

Preparation of L-menthyl cis-1,3-oxathiolan-5-hydroxy-2-carboxylate

A mixture of aqueous glyoxalic acid (200 g; 50% w/v), L-menthol (632.4 g) and concentrated sulfuric acid (3.5 g) in cyclohexane (600 mL) was refluxed at 80° C. to 85° C. for 3 to 4 hours. Water (115 mL) was removed by azeotropic distillation using a Dean Stark trap. The resulting solution was allowed to cool to room temperature and diluted with de-ionized water (500 mL). The organic layer was separated and diluted with de-ionized water (800 mL). The pH of the resultant mixture was adjusted to 5 using aqueous sodium carbonate (10%; 15 ml). The organic layer was separated and washed twice with aqueous sodium bisulfite (2×70 g in 2×800 mL of de-ionized water). The pH of the organic layer was again adjusted to 5 using aqueous sodium carbonate (10%; 20 ml) and aqueous solution of formaldehyde (130 mL) was added to it in one hour at room temperature. The pH of the resultant mixture was again adjusted to 7.5 using aqueous sodium carbonate (10%; 15 ml) and stirred for about 6 hours at room temperature. The suspension obtained was filtered and washed with de-ionized water (2×200 mL) at room temperature. The wet mass obtained was suspended in de-ionized water (1000 mL) and stirred for 2 hours at 40° C. to 45° C. The resultant mixture was cooled to 20° C. to 25° C. and stirred at the same temperature for one hour. The suspension was filtered and washed with de-ionized water (200 mL) at room temperature to give menthyl glyoxalate as wet mass.

Weight of wet mass: 290 g.

The menthyl glyoxalate (wet mass; 290 g) obtained above was stirred in toluene (1400 mL) at 40° C. to 45° C. for 15 minutes. The resultant mixture was diluted with de-ionized water (600 mL) and stirred for 15 minutes at 40° C. to 45° C. Organic layer was separated and washed with de-ionized water (600 mL). The organic layer was refluxed at 110° C. to 112° C. and water (~9 mL) was azeotropically removed using a Dean Stark trap.

The reaction mixture was allowed to cool to room temperature. 1,4-Dithian-2,5-diol (78 g) was added to the reaction mixture at room temperature and refluxed at 110° C. to 112° C. for about 2 hours. After completion of the reaction, the mixture was allowed to cool to room temperature, filtered through Hyflo bed and washed with toluene (100 mL). The filtrate was concentrated under vacuum at 45° C. to 50° C. to give a residue. Toluene (300 mL) was added to the residue and stirred at room temperature for 10 minutes. To this solution was added a mixture of hexanes (1200 mL) and triethylamine (20 mL) in 2 hours at room temperature and the resultant mixture was stirred at the same temperature for about 3 hours. The reaction mixture was cooled to 0° C. to 5° C. and stirred at same temperature for about 6 hours. The product was filtered and washed with pre cooled (0° C. to 5° C.) hexanes (375 mL).

Weight: 230 g

Example 2

L-menthyl 1,3-oxathiolan-5S-(5-fluorocytosin-1-yl)-2R-carboxylate oxalate

A) Preparation of L-menthyl cis-1,3-oxathiolan-5-chloro-2-carboxylate

Thionyl chloride (80 ml) was added to a mixture of L-menthyl cis-1,3-oxathiolan-5-hydroxy-2-carboxylate (300 g; Example 1), methane sulphonic acid (1 ml) and dimethylformamide (85 ml) in dichloromethane (900 ml) at 5° C. to 10° C. and stirred for about 3 hours at 10° C. to 15° C. After completion of the reaction, the reaction mixture was diluted with de-ionized water (300 mL) and stirred for 30 minutes at 20° C. to 25° C. The organic layer was separated, washed with de-ionized water (300 mL) and concentrated at 40° C. to 45° C. at reduced pressure of 650 to 700 mm of Hg to give L-menthyl cis-1,3-oxathiolan-5-chloro-2-carboxylate which was taken to the next step without any purification.

Weight: 300 g

B) Preparation of 5-fluoro-N-(trimethylsilyl)-2-[(trimethylsily)oxy]pyrimidin-4-amine A mixture of 5-Fluorocytosine (100 g) and ammonium sulphate (5 g) in hexamethyl disilazane (200 ml) was refluxed at 125° C. to 130° C. for 4 hours to give a clear solution. The resulting solution was allowed to cool to room temperature and diluted with dichloromethane (300 mL). Trimethyl amine (140 mL) was added to the resulting solution in 30 minutes at 20° C. to 25° C. and was stirred at same temperature for about 30 minutes. The solution containing 5-fluoro-N-(trimethylsilyl)-2-[(trimethylsilyl)oxy]pyrimidin-4-amine was kept at 20° C. to 25° C. for further use.

C) L-menthyl 1,3-oxathiolan-5S-(5-fluorocytosin-1-yl)-2R-carboxylate oxalate

A solution of L-menthyl cis-1,3-oxathiolan-5-chloro-2-carboxylate (entire batch; Example 2A) in dichloromethane (300 mL) was added to (5-fluoro-N-(trimethylsilyl)-2-[(trimethylsilyl)oxy]pyrimidin-4-amine (Example 2 B) at 40° C. to 45° C. in one hour and the mixture was refluxed at 40° C. to 45° C. for about 18 hours. After completion of the reaction, the mixture was allowed to cool to room temperature, diluted with de-ionized water (500 mL) and stirred at the same temperature for about 30 minutes. The organic layer was treated with concentrated hydrochloric acid (1 mL), diluted with de-ionized water (500 mL) and washed with aqueous solution of sodium chloride (10%; 500 mL). The organic layer was then concentrated at 40° C. to 45° C. under reduced pressure (650 to 700 mm of Hg) for one hour. The residue obtained was dissolved in methanol (2000 mL) at 40° C. to 45° C., treated with oxalic acid (100 g) and stirred for 30 minutes at 40° C. The reaction mixture was allowed to cool to room temperature and stirred at the same temperature for one hour. The temperature was raised to 65° C. to 70° C. and the reaction mixture was stirred at this temperature for 30 minutes. The reaction mixture was allowed to cool to room temperature and stirred at room temperature for 2 hours. Finally, the reaction mixture was cooled to 0° C. to 5° C. and stirred at the same temperature for 3 hours. The precipitates obtained were filtered at 0° C. to 5° C., washed with ethyl acetate (400 mL) at room temperature and dried under reduced pressure.

Weight: 300 g

Example 3

Preparation of emtricitabine hydrochloride

Aqueous sodium carbonate (63.4 g in 562.5 mL of de-ionized water) was added to a solution of L-menthyl 1,3-oxathiolan-5S-(5-fluorocytosin-1-yl)-2R-carboxylate oxalate (225 g) in a mixture of dichloromethane (1700 mL) and de-ionized water (562.5 mL) and was stirred for 30 minutes at 25° C. to 30° C. The organic layer was separated and washed with de-ionized water (1125 mL) at 25° C. to 30° C. and concentrated at 40° C. to 45° C. under atmospheric pressure. Denatured spirit (450 mL) was added to the resulting residue at 40° C. to 45° C. and the mixture was concentrated under vacuum for about one hour to get a residue. The residue obtained was dissolved in denatured spirit (1575 mL) and the solution was cooled to 15° C. to 20° C. Aqueous di-potassium hydrogen phosphate (270 g in 450 mL of de-ionized water) was added to a solution of the residue in de-natured spirit and stirred for 30 minutes at 15° C. to 20° C. A solution of sodium borohydride (36 g) and aqueous sodium hydroxide (4.5 mL; 30% in 225 mL de-ionized water) was added and stirred for 2 to 3 hours at 20° C. to 25° C. After completion of the reaction, the pH of the organic layer was adjusted to 4.0 to 4.5 using concentrated hydrochloric acid (10 mL) and stirred for one hour at 25° C. to 30° C. and then adjusted to 6.8 to 7.2 using aqueous sodium hydroxide (30%; 8 mL). The organic layer was concentrated under reduced pressure at 45° C. to 50° C. to get an oily residue. The oily residue was dissolved in absolute ethanol (450 mL) and concentrated under vacuum at 45° C. to 50° C. The residue obtained was again dissolved in absolute ethanol (450 mL) at 45° C. to 50° C. and concentrated under vacuum at 45° C. to 50° C. Isopropyl alcohol (900 mL) was added to the residue and refluxed at 80° C. to 82° C. for 30 minutes. The resulting solution was treated with activated carbon (11.25 g) and heated to 70° C. to 75° C. The resulting hot mixture (at ~70° C. to 75° C.) was filtered using a Hyflo bed. The Hyflo bed was washed with isopropanol (112.5 mL) at 75° C. to 78° C. and the filtrate was allowed to cool to 25° C. to 30° C. Isopropyl alcohol saturated with hydrochloric acid (142.08 g of hydrochloric acid in 1000 mL of isopropyl alcohol) was added to the filtrate at 25° C. to 30° C. in one hour and stirred at the same temperature for about 4 hours. The product was filtered, washed with isopropyl alcohol (112.5 mL) and dried under vacuum at 40° C. to 45° C.

Weight: 101 g

Example 4

Preparation of emtricitabine (crude)

Tri-n-butyl amine (76.76 g) was added to a solution of emtricitabine hydrochloride (101 g; Example 3) in dichloromethane (450 mL) in 30 minutes at 25° C. to 30° C. The solution was stirred at 25° C. to 30° C. for about 5 hours. The product was filtered, washed with dichloromethane (112.5 mL) and dried under vacuum at 40° C. to 45° C. for about 14 hours.

Weight: 80 g

Example 5

Preparation of emtricitabine (pure)

Activated carbon (4.0 g) was added to the solution of crude emtricitabine (Example 4; 75 g) in isopropyl alcohol (1000 mL) at 80° C. to 82° C. and stirred for 30 minutes at the same temperature. The solution was filtered through a Hyflo bed at 75° C. to 80° C. and washed with isopropyl alcohol (40 mL). The filtrate was allowed to cool to 20° C. to 25° C. and stirred at the same temperature for 5 to 6 hours. The product was filtered, washed with isopropyl alcohol (80 mL) at 20° C. to 25° C. and dried under vacuum at 40° C. to 45° C.

Weight: 60 g
Purity (By HPLC): 99.86%

We claim:

1. A process for the preparation of emtricitabine of Formula I,

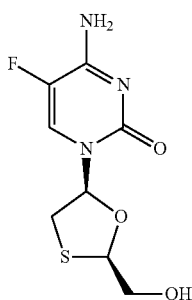

Formula I comprising the steps of:
a) salifying compound of Formula II;

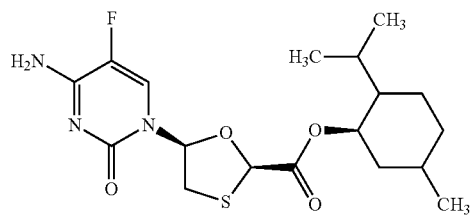

Formula II b) reducing the salt obtained in step (a) in the presence of a phosphate buffer;

c) isolating emtricitabine as salt;

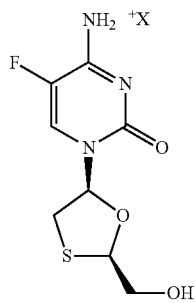

Formula III wherein, 'X' is anion of an acid,
d) recovering emtricitabine as free base using tri-n-butylamine.

2. The process according to claim 1, wherein the compound of Formula II is salified using an organic or inorganic acid.

3. The process according to claim 1, wherein reduction is carried out using a reducing agent selected from a group consisting of metal hydride reagents or boranes.

4. The process according to claim 1, wherein emtricitabine is isolated as an organic or inorganic acid salt.

5. A process for the preparation of emtricitabine of Formula I,

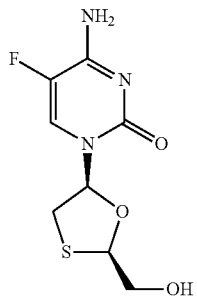

Formula I comprising the steps of:
a) reacting 5-fluorocytosine derivative of Formula IV,

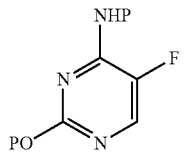

Formula IV wherein 'P' is hydrogen or protecting group,
with a 1,3-oxathiolane derivative of Formula V,

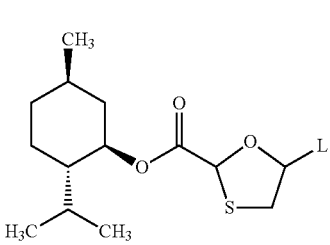

Formula V wherein 'L' is a leaving group, to give a compound of Formula II,

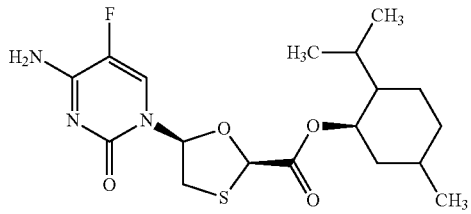

Formula II b) salifying the compound of Formula II;
c) reducing the salt obtained in step (b) in the presence of a phosphate buffer;
d) isolating emtricitabine as its salt;

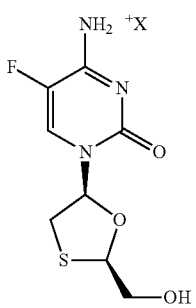

Formula III wherein, 'X' is anion of an acid,
e) recovering emtricitabine free base, using tri-n-butylamine.

6. The process according to claim 5, wherein 'P' is an alkyl silyl group.

7. The process according to claim 5, wherein 'P' is a trimethyl silyl group.

8. The process according to claim 5, wherein 'L' is a leaving group selected from a group consisting of halogens.

9. The process according to claim 8, wherein 'L' is chlorine.

10. The process according to claim 5, wherein the compound of Formula II is salified using an organic or inorganic acid.

11. The process according to claim 10, wherein an organic acid is selected from a group consisting of acetic acid, lactic acid, salicylic acid, citric acid, tartraric acid, bitartraric acid, ascorbic acid, oxalic acid, succinic acid, maleic acid, fumaric acid, benzoic acid, glutamic acid, methanesulfonic acid, ethanesulfonic acid, benzensulfonic acid or p-toluenesulfonic acid.

12. The process according to claim 11, wherein an organic acid is oxalic acid.

13. The process according to claim 5, wherein reduction is carried out using a reducing agent selected from a group consisting of metal hydride reagents or boranes.

14. The process according to claim 13, wherein reduction is carried out using metal hydride.

15. The process according to claim 14, wherein reduction is carried out using sodium borohydride.

16. The process according to claim 5, wherein emtricitabine is isolated as an organic or inorganic acid salt.

17. The process according to claim 16, wherein emtricitabine is isolated as a hydrochloride.

* * * * *

UNITED STATES PATENT AND TRADEMARK OFFICE
CERTIFICATE OF CORRECTION

PATENT NO.     : 8,748,604 B2
APPLICATION NO. : 13/582513
DATED          : June 10, 2014
INVENTOR(S)    : Prakash Bhimaji Kshirsagar et al.

Page 1 of 1

It is certified that error appears in the above-identified patent and that said Letters Patent is hereby corrected as shown below:

In the specification

COLUMN 5, LINE 10:

"acid citric acid, oxalic acid, tartraric acid, pantothenoic acid, should read

-- acid, citric acid, oxalic acid, tartaric acid, pantothenoic acid --

COLUMN 5, LINE 44:

"known to the a person skilled in the art to separate solid"

should read

-- known to a person skilled in the art to separate solid --

In the claims

COLUMN 12, LINES 4-5, CLAIM 7:

"7. The process according to claim 5, wherein 'P' is a trimethyl silyl group."

should read

-- 7. The process according to claim 6, wherein 'P' is a trimethyl silyl group. --

Signed and Sealed this
Sixth Day of October, 2015

Michelle K. Lee
*Director of the United States Patent and Trademark Office*